United States Patent
Haning et al.

(10) Patent No.: US 6,803,480 B2
(45) Date of Patent: Oct. 12, 2004

(54) DIPHENYLMETHANE DERIVATIVES

(75) Inventors: Helmut Haning, Wuppertal (DE);
Gunter Schmidt, Wuppertal (DE);
Josef Pernerstorfer, Wuppertal (DE);
Hilmar Bischoff, Wuppertal (DE);
Carsten Schmeck, Wuppertal (DE);
Verena Vöhringer, Wuppertal (DE);
Michael Woltering, Wuppertal (DE);
Axel Kretschmer, Wuppertal (DE);
Christiane Faeste, Haan (DE)

(73) Assignee: Bayer Aktiengesellschaft, Leverkusen (DE)

(*) Notice: Subject to any disclaimer, the term of this patent is extended or adjusted under 35 U.S.C. 154(b) by 20 days.

(21) Appl. No.: 10/276,447

(22) PCT Filed: May 7, 2001

(86) PCT No.: PCT/EP01/05142
§ 371 (c)(1),
(2), (4) Date: Mar. 11, 2003

(87) PCT Pub. No.: WO01/90053
PCT Pub. Date: Nov. 29, 2001

(65) Prior Publication Data
US 2003/0203898 A1 Oct. 30, 2003

(30) Foreign Application Priority Data
May 19, 2000 (DE) .......................... 100 24 939

(51) Int. Cl.$^7$ .............................................. C67C 69/76
(52) U.S. Cl. .............................. 560/57; 560/58; 560/15; 560/16; 562/426; 562/468; 514/534; 514/557; 568/162
(58) Field of Search .............................. 560/57, 58, 15, 560/16; 514/534, 557; 564/162, 426, 468

(56) References Cited

FOREIGN PATENT DOCUMENTS

| EP | 0188351 | 7/1986 |
|---|---|---|
| EP | 0580550 | 1/1994 |
| WO | 9857919 | 12/1998 |
| WO | 9926966 | 6/1999 |

OTHER PUBLICATIONS

Koehrle, J et al, Journal of Biological Chem. (1986) 261(25) 11613–22.*
Bres, O. et al General and Comparative Endocrinology (1986) 61(1) 29–39.*
Frieden, E et al, General and Comparaive Endocrinology (1978) 36(2) 215–22.*
Snyder, S et al International Congress Series (1976) 378 (Thyroid Res.) 297–9.*

* cited by examiner

*Primary Examiner*—Paul J. Killos

(57) ABSTRACT

The invention relates to novel diphenylmethane derivatives, processes for their preparation and their use in medicaments, in particular for the indications of arteriosclerosis and hypercholesterolaemia.

12 Claims, No Drawings

DIPHENYLMETHANE DERIVATIVES

The invention relates to novel diphenylmethane derivatives, processes for their preparation and their use in medicaments, in particular for the indications of arteriosclerosis and hypercholesterolaemia.

European application 580 550 A describes oxamic acid derivatives having cholesterol-lowering properties in mammals. This application describes an in vitro test based on the binding of thyroid hormone cell receptors (called $T_3$ nuclear receptors). Some of the compounds described therein are stated to have IC-50 values of 0.2 nM and 0.1 nM in the L-triiodothyronine ($LT_3$) nuclear receptor test. The pharmacological property which is emphasized is the reduction in plasma cholesterol, in particular LDL-cholesterol. Cholesterol-lowering effects are also described in the European application EP-A-188 351 for certain diphenyl ethers with thyroid hormone-like effects.

Tripp et al. in J. Med. Chem. 1973, 16(1), 60–64 describe the synthesis of methylene- and carbonyl-bridged analogs of iodothyronine. They found that their thyromimetic activity was less than that of the corresponding O- or S-bridged compounds.

Psychoyos et al. in Endocrinology 1973, 92(1), 243–250 also investigated the thyromimetic activity of methylene-bridged thyroid hormone analogs. They likewise concluded that the methylene-bridged compounds were less potent than the O-bridged compounds.

WO 98/57919 discloses selective thyroid hormone agonists with a diphenylmethane basic structure and their use in medicaments.

WO 99/26966 describes novel methods for designing ligands which bind to certain receptors (called "nuclear receptors"). It is reported in particular that molecules suitable for modulating the thyroid receptor must comply with certain three-dimensional requirements.

The invention relates to diphenylmethane derivatives of the general formula (I)

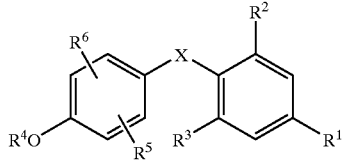

in which
X is $CH_2$, CHF or $CF_2$,
$R^1$ is a group of the formula

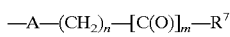

in which
A is $CH_2$, S, C(O) or $NR^8$,
n is the number 0, 1, 2 or 3,
m is the number 1 or 2,
where m is the number 2 in the case where $R^2$ and $R^3$ are halogen,
$R^7$ is $(C_1-C_6)$-alkyl or a radical of the formula $-NR^9R^{10}$ or $-OR^{11}$,
in which
$R^8$, $R^9$, $R^{10}$ and $R^{11}$ are identical or different and are, independently of one another, hydrogen, $(C_1-C_6)$-alkyl or $(C_1-C_8)$-cycloalkyl,
$R^2$ and $R^3$ are identical or different and are halogen, $(C_1-C_6)$-alkyl, $(C_3-C_7)$-cycloalkyl, vinyl, $CF_3$, $CHF_2$ or $CH_2F$, $R^4$ is hydrogen, $(C_1-C_6)$-alkyl or $(C_1-C_6)$-acyl,
$R^5$ is hydrogen, halogen, hydroxyl, cyano, $CF_3$, $(C_1-C_6)$-alkyl or $(C_1-C_6)$-alkoxy,
$R^6$ is a radical of the formula

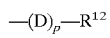

in which
D is a group of the formula

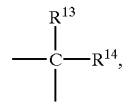

in which
$R^{13}$ and $R^{14}$ together are an oxo group or are identical or different and are hydrogen, halogen, hydroxyl, $(C_1-C_6)$-alkyl, $(C_1-C_6)$-alkoxy or a radical of the formula $-NR^{15}R^{16}$,
in which
$R^{15}$ and $R^{16}$ are identical or different and are hydrogen, benzyl, $(C_1-C_6)$-alkyl or $(C_3-C_8)$-cycloalkyl,
p is the number 0 or 1,
and
$R^{12}$ is hydrogen, $OR^{17}$, $NR^{18}R^{19}$, $(C_1-C_8)$-alkyl, $(C_3-C_8)$-cycloalkyl, $(C_6-C_{10})$-aryl or a saturated, unsaturated or aromatic 5- to 10-membered heterocycle with up to three identical or different heteroatoms from the series of S, O and/or N,
where
the aforementioned hydrocarbon radicals and heterocycles may optionally be substituted once to three times, identically or differently, by substituents from the group of halogen, hydroxyl, oxo, cyano, nitro, amino, $CF_3$, $(C_1-C_6)$-alkyl, $(C_1-C_6)$-alkoxy, $(C_3-C_8)$-cycloalkyl, $-O-C(O)-R^{20}$, $-C(O)-O-R^{21}$, $-C(O)-NR^{22}R^{23}$ or $-NH-C(O)-O-R^{24}$,
and
in which
$R^{17}$, $R^{18}$, $R^{19}$, $R^{20}$, $R^{21}$, $R^{22}$, $R^{23}$ and $R^{24}$ are identical or different and are each, independently of one another, hydrogen, $(C_1-C_6)$-alkyl or $(C_3-C_8)$-cycloalkyl, each of which in turn may be substituted by hydroxyl, amino, mono- or di-$(C_1-C_6)$-alkylamino, phenyl, a saturated, unsaturated or aromatic 5- to 10-membered heterocycle with up to three identical or different heteroatoms from the series of S, O and/or N,
and the salts thereof.

Heterocycles which may be preferably mentioned in the definition of $R^{12}$ and $R^{17}$ to $R^{24}$ are:

A 5- to 8-membered saturated, partly unsaturated or aromatic, optionally benzo-fused heterocycle with up to 4 heteroatoms from the series of S, N and/or O, i.e. a heterocycle which may contain one or more double bonds and which is linked via a ring carbon atom or a ring nitrogen atom. Examples which may be mentioned are: tetrahydrofur-2-yl, tetrahydrofur-3-yl, pyrrolidin-1-yl, pyrrolidin-2-yl, pyrrolidin-3-yl, pyrrolin-1-yl, piperidin-1-yl, piperidin-3-yl, 1,2-dihydropyridin-1-yl, 1,4-dihydropyridin-1-yl, piperazin-1-yl, morpholin-1-yl, azepin-1-yl, 1,4-diazepin-1-yl, furan-2-yl, furan-3-yl, pyrrol-1-yl, pyrrol-2-yl, pyrrol-3-yl, thienyl, thiazolyl, oxazolyl, imidazolyl, triazolyl, tetrazolyl, pyridyl, pyrimidyl, pyrazinyl, pyrimidinonyl, pyridazinonyl.

Preference is given to the following from this list: pyridyl, pyrimidyl, pyridazinyl, pyrimidinonyl, pyridazinonyl.

$(C_1–C_8)$-Alkyl, $(C_1–C_6)$-alkyl, $(C_1–C_4)$-alkyl and $(C_1–C_3)$-alkyl are for the purposes of the invention a straight-chain or branched alkyl radical respectively with 1 to 8, 1 to 6, 1 to 4 and 1 to 3 carbon atoms. A straight-chain or branched alkyl radical with 1 to 3 carbon atoms is preferred. Examples which may be mentioned are: methyl, ethyl, n-propyl, isopropyl, t-butyl, n-pentyl and n-hexyl.

$(C_6–C_{10})$-Aryl is for the purposes of the invention an aromatic radical with 6 to 10 carbon atoms. Preferred aryl radicals are phenyl and naphthyl.

$(C_3–C_8)$-Cycloalkyl, $(C_3–C_7)$-cycloalkyl and $(C_3–C_6)$-cycloalkyl are for the purposes of the invention a cycloalkyl group respectively with 3 to 8, 3 to 7 and 3 to 6 carbon atoms. Those which may be mentioned as preferred are: cyclopropyl, cyclobutyl, cyclopentyl, cyclohexyl and cycloheptyl.

$(C_1–C_6)$-Alkoxy is for the purposes of the invention a straight-chain or branched alkoxy radical with 1 to 6 carbon atoms. A straight-chain or branched alkoxy radical with 1 to 3 carbon atoms is preferred. Examples which may be mentioned are: methoxy, ethoxy, n-propoxy, isopropoxy, t-butoxy, n-pentoxy and n-hexoxy.

$(C_1–C_6)$-Acyl is for the purposes of the invention particularly a straight-chain or branched alkyl radical with 1 to 6 carbon atoms which has a doubly bonded oxygen atom in the 1 position and is linked via the 1 position. Examples which may be mentioned are: formyl, acetyl, propionyl, n-butyryl, i-butyryl, pivaloyl, n-hexanoyl.

Halogen includes for the purposes of the invention fluorine, chlorine, bromine and iodine. Fluorine, chlorine or bromine are preferred.

The compounds according to the invention may, depending on the substitution pattern, exist in stereoisomeric forms which either are related as image and mirror image (enantiomers) or are not related as image and mirror image (diastereomers). The invention relates both to the enantiomers or diastereomers and to respective mixtures thereof. The racemic forms can, just like the diastereomers, be separated into the stereoisomerically pure constituents in a known manner.

Certain compounds may furthermore exist in tautomeric forms. This is known to the skilled person, and such compounds are likewise encompassed by the scope of the invention.

The compounds according to the invention may also be in the form of salts. Physiologically acceptable salts are preferred for the purposes of the invention.

Physiologically acceptable salts may be salts of the compounds according to the invention with inorganic or organic acids. Preference is given to salts with inorganic acids such as, for example, hydrochloric acid, hydrobromic acid, phosphoric acid or sulphuric acid, or salts with, organic carboxylic or sulphonic acids such as, for example, acetic acid, propionic acid, maleic acid, fumaric acid, malic acid, citric acid, tartaric acid, lactic acid, benzoic acid, or methanesulphonic acid, ethane-sulphonic acid, benzenesulphonic acid, toluenesulphonic acid or naphthalenedisulphonic acid.

Physiologically acceptable salts may likewise be salts of the compounds according to the invention with bases, such as, for example, metal or ammonium salts. Preferred examples are alkali metal salts (for example sodium or potassium salts), alkaline earth metal salts (for example magnesium or calcium salts), and ammonium salts which are derived from ammonia or organic amines such as, for example, ethylamine, di- or triethylamine, ethyldiisopropylamine, ethanolamine, di- or triethanolamine, dicyclohexylamine, dimethylaminoethanol, dibenzylamine, N-methylmorpholine, dihydroabietylamine, 1-ephenamine, methylpiperidine, arginine, lysine, ethylenediamine or 2-phenylethylamine.

The compounds according to the invention may also be in the form of their solvates, in particular in the form of their hydrates.

Preference is given to compounds of the general formula (I)

in which

X is $CH_2$, CHF or $CF_2$, $R^1$ is a group of the formula

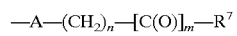

in which

A is $CH_2$, C(O) or $NR^8$, n is the number 0, 1 or 2, m is the number 1 or 2, where m is the number 2 in the case where $R^2$ and $R^3$ are halogen, or A is $CH_2$, and n is not the number 1 when A is NH m is the number 1 and, $R^7$ is a radical of the formula $—NR^9R^{10}$ or $—OR^{11}$, in which $R^8$, $R^9$, $R^{10}$ and $R^{11}$ are identical or different and, independently of one another, are hydrogen, $(C_1–C_6)$-alkyl or $(C_3–C_8)$-cycloalkyl, $R^2$ and $R^3$ are identical or different and are halogen, $(C_1–C_6)$-alkyl, cyclopropyl, vinyl, $CF_3$, $CHF_2$ or $CH_2F$, $R^4$ is hydrogen, $(C_1–C_3)$-alkyl or $(C_1–C_3)$-acyl, $R^5$ is hydrogen, halogen, $CF_3$, $(C_1–C_3)$-alkyl or $(C_1–C_3)$-alkoxy, $R^6$ is a radical of the formula

in which

D is a group of the formula

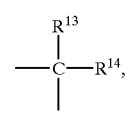

in which $R^{13}$ and $R^{14}$ together are an oxo group or are identical or different and are hydrogen, hydroxyl, $(C_1–C_6)$-alkyl, p is the number 0 or 1, and $R^{12}$ is hydrogen, $OR^{17}$, $NR^{18}R^{19}$, $(C_1–C_8)$-alkyl, $(C_3–C_8)$-cycloalkyl, $(C_6–C_{10})$-aryl or a saturated, unsaturated or aromatic 5- to 6-membered heterocycle with up to three identical or different heteroatoms from the series of S, O and/or N, where the aforementioned hydrocarbon radicals and heterocycles may optionally be substituted once to three times, identically or differently, by substituents from the group of halogen, hydroxyl, oxo, cyano, nitro, amino, $CF_3$, $(C_1–C_6)$-alkyl, $(C_1–C_6)$-alkoxy, ($C_3$–$C_8$)-cycloalkyl, —O—C(O)—$R^{20}$, —C(O)—O—$R^{21}$, —C(O)—$NR^{22}R^{23}$ or —NH—C(O)—O—$R^{24}$, and in which $R^{17}$, $R^{18}$, $R^{19}$, $R^{20}$, $R^{21}$, $R^{22}$, $R^{23}$ and $R^{24}$ are identical or different and are each, independently of one another, hydrogen, ($C_1$–$C_6$)-alkyl or ($C_3$–$C_8$)-cycloalkyl, each of which in turn may be substituted by hydroxyl, amino, mono- or di-($C_1$–$C_6$)-alkylamino, phenyl, a saturated, unsaturated or aromatic 5- to 6-membered heterocycle with up to three identical or different heteroatoms from the series of S, O and/or N, and the salts thereof.

Of particular importance are compounds of the general formula (I)

in which

X is $CH_2$, CHF or $CF_2$, $R^1$ is a group of the formula —NH—C(O)—C(O)—$OR^{11}$, in which $R^{11}$ is hydrogen or ($C_1$–$C_4$)-alkyl, $R^2$ and $R^3$ are identical or different and are halogen, ($C_1$–$C_4$)-alkyl, cyclopropyl, $CF_3$, $CHF_2$ or $CH_2F$, $R^4$ is hydrogen or ($C_1$–$C_3$)-alkyl, $R^5$ is hydrogen, and $R^6$ is ($C_1$–$C_6$)-alkyl or ($C_3$–$C_6$)-cycloalkyl or is a radical of the formula

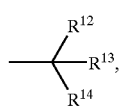

in which $R^{12}$ is phenyl, pyrimidinyl, pyridyl or 3(2H)-pyridazinonyl, each of which may be substituted up to three times, identically or differently, by halogen, hydroxyl, trifluoromethyl, ($C_1$–$C_3$)-alkyl or ($C_1$–$C_3$)-alkoxy, or is a radical of the formula —$NR^{18}R^{19}$, in which $R^{18}$ and $R^{19}$ are identical or different and are, independently of one another, ($C_1$–$C_4$)-alkyl which may be substituted by hydroxyl, amino, mono- or di-($C_1$–$C_4$)-alkylamino, or by phenyl, pyridyl or pyrimidinyl, each of which is optionally substituted up to three times by hydroxyl, halogen, trifluoromethyl, methoxy or ($C_1$–$C_3$)-alkyl, $R^{13}$ and $R^{14}$ together are an oxo group or are identical or different and are hydrogen, hydroxyl, ($C_1$–$C_6$)-alkyl, and the salts thereof.

Preferred compounds of the formula (I) are those in which $R^2$ and $R^3$ are methyl.

Preferred compounds of the formula (I) are those in which $R^5$ is hydrogen. Preferred compounds of the formula (I) are those in which $R^4$ is methyl or hydrogen. The compounds according to the invention of the general formula (I) can be prepared by reacting reactive phenol derivatives of the general formula (II) with reactive phenyl derivatives of the general formula (III)

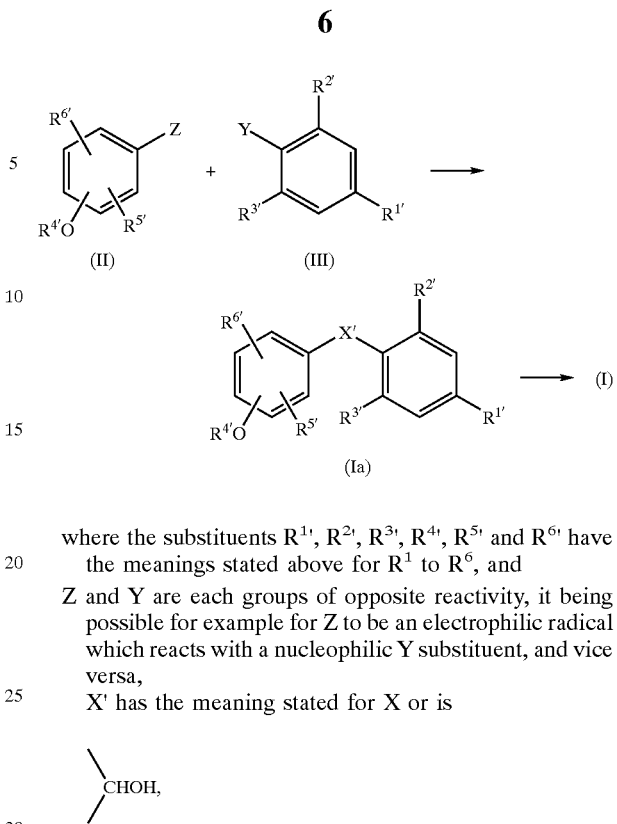

where the substituents $R^{1'}$, $R^{2'}$, $R^{3'}$, $R^{4'}$, $R^{5'}$ and $R^{6'}$ have the meanings stated above for $R^1$ to $R^6$, and Z and Y are each groups of opposite reactivity, it being possible for example for Z to be an electrophilic radical which reacts with a nucleophilic Y substituent, and vice versa, X' has the meaning stated for X or is

where appropriate in the presence of inert solvents and catalysts and, where appropriate, with isolation of the intermediates of the general formula (Ia) in which X' is —CH(OH)— or directly to give compounds of the formula (I).

Examples of catalysts which may be mentioned are coupling catalysts such as Pd compounds and/or Cu compounds.

Examples which may be mentioned of reactive groups Z and Y are: formyl, $CH_2$Hal (Hal=halogen, in particular Cl, Br or I), $CH_2$OTosyl, Li, MgHal, and derivatives of Cu, Pd, Sn or boron.

The phenol derivatives of the general formula (II) which can be employed according to the invention are known or can be prepared by known methods (compare, for example, Chemistry & Biology 1998, 5, 299–306, J. Org. Chem. 1956, 21, 1458).

The phenyl derivatives of the general formula (III) are likewise known or can be prepared by known methods (compare, for example, J. Med. Chem. 1997, 40, 3542–3550 and the references stated above for the phenol derivatives of the formula (II)).

The reaction of the starting compounds (II) with (III) generally proceeds under atmospheric pressure. However, it can also be carried out under elevated or reduced pressure.

The reaction can be carried out in a temperature range from –100° C. to 200° C., preferably between –78° C. and 150° C. in the presence of inert solvents. Inert solvents which may be mentioned as preferred are: dimethyl sulphoxide (DMSO), dimethylformamide (DMF), tetrahydrofuran (THF), diethyl ether etc.

Depending on the specific substitution pattern, the reaction of (II) and (III) may also result in intermediates of the formula (Ia) in which X' is a CHOH group, which can then be reduced, with or without isolation of these intermediates, by conventional methods to the corresponding methylene group.

The process according to the invention can be illustrated by way of example by the following formula diagrams:

Process Variant (A)

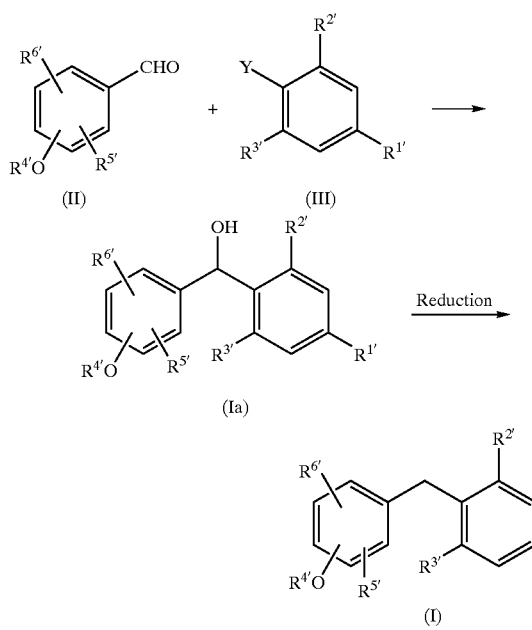

Process Variant (B)

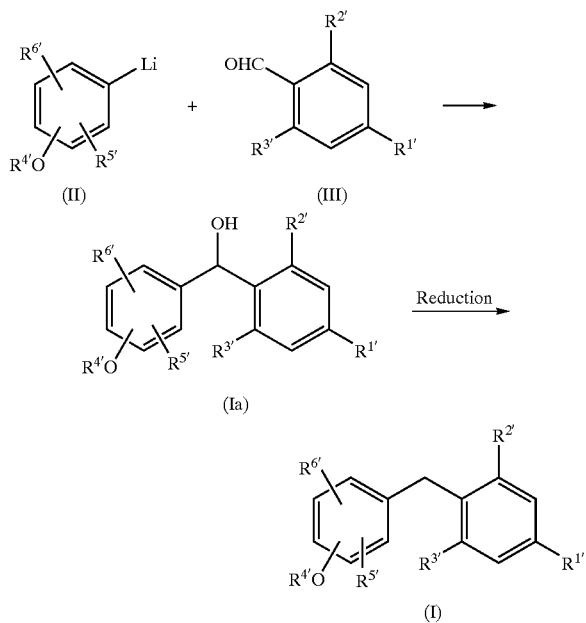

Depending on the meaning of the substituents $R^{1'}$, $R^{2'}$, $R^{4'}$, $R^{5'}$, and $R^{6'}$ it may be sensible or necessary for them to be varied at individual stages of the process within the stated scope of the meanings. Intermediate protection with conventional protective groups may also be necessary for particular substituents, which are liberated again at a later stage by elimination of the protective group.

Protective groups mean in the present application those groups which, in starting, intermediate and/or final products, protect functional groups which, are present, such as, for example, carboxyl, amino or hydroxyl groups, and which are customary in preparative organic chemistry. The groups protected in this way can then be converted into free functional groups in a simple manner under known conditions.

This invention likewise relates to the precursors or intermediates of the formula (Ia), in which X' is —CH(OH)— and which occur in the reaction of (II) and (III). They have essential structural features of the compounds according to the invention of the formula (I) and their prodrugs and thus meet all the requirements for patenting as novel intermediates.

The compounds according to the invention of the formula (I) show a surprising and valuable range of pharmacological actions and can therefore be employed as versatile medicaments. In particular, they can be employed for all indications which can be treated with natural thyroid hormones, such as, for example and preferably, depression, goitre or thyroid cancer. It is possible and preferred to use the compounds according to the invention of the formula (I) to treat arteriosclerosis, hypercholesterolaemia and dyslipidaemia. It is additionally possible to treat adiposity and corpulence (obesity) and heart failure, and achieve a postprandial reduction in triglycerides.

The compounds are also suitable for the treatment of certain airway disorders, in particular pulmonary emphysemas, and for medically promoting maturation of the lungs.

The compounds are also suitable for the treatment of Alzheimer's disease.

The compounds are furthermore suitable for the treatment of osteoporosis, cardiac arrhythmias, hypothyroidism and skin disorders.

The compounds can additionally be employed for the promotion and regeneration of hair growth.

The active substances according to the invention open up a further treatment alternative and represent an enrichment of pharmacy. Compared with known and previously employed thyroid hormone products, the compounds according to the invention show an improved range of action. They are preferably distinguished by great specificity, good tolerability and fewer side effects, in particular in the cardiovascular area.

Their activity can be tested, for example, in vitro by the following T3 promoter assay cell test:

The test is carried out with a stably transfected human HepG2 hepatocarcinoma cell which expresses a luciferase gene under the control of a thyroid hormone-regulated promoter. The vector used for the transfection has upstream of the luciferase gene a minimal thymidine kinase promoter with a thyroid hormone-responsive element (TRE) which consists of two inverted palindromes each of 12 bp and of an 8 bp spacer.

For the test, the cell cultures are seeded in Eagle's minimal essential medium in 96-well plates with the following additions: glutamine, tricine, sodium pyruvate, non-essential amino acids, insulin, selenium and transferrin. The cultures are grown at 37° C. with a 10% $CO_2$ atmosphere for 48 hours. Then serial dilutions of test substance or reference compound (T3, T4) and costimulator retinoic acid are added to the test cultures and the latter are incubated as previously for a further 48 or 72 hours. Each substance concentration is tested in four replicates. To determine the luciferase induced by T3 or other substances, the cells are subsequently lysed by adding a Triton- and luciferin-containing buffer and measured immediately in a luminometer. The $EC_{50}$ values for each compound are calculated (see Table 1).

TABLE 1

| Example | EC$_{50}$ [nM] |
|---------|----------------|
| 2 | 0.14 |
| 4 | 0.23 |
| 5 | 4.3 |

The compounds according to the invention also show surprisingly advantageous properties in the in vivo test described below:

Description of test for finding pharmacologically active substances which lower the serum cholesterol in mice:

The substances to be investigated for their serum cholesterol-lowering effect in vivo are administered orally to male mice with a body weight between 25 and 35 g. One day before starting the test, the animals are divided into groups with an identical number of animals, usually n=7–10. Throughout the test drinking water and feed are available ad libitum to the animals. The substances are administered orally once a day for 7 days. For this purpose, the test substances are dissolved in a solution of Solutol HS 15+ethanol+saline (0.9%) in the ratio 1+1+8 or in a solution of Solutol HS 15+saline (0.9%) in the ratio 2+8. The dissolved substances are administered by gavage in a volume of 10 ml/kg of body weight. Animals treated in exactly the same way but receiving only the solvent (10 ml/kg of body weight) without test substance serve as control group.

Before the first administration of substance, blood is taken from each mouse by puncture of the retroorbital venous plexus for determination of the serum cholesterol (initial value). The test substance is then administered to the animals by gavage for the first time. 24 hours after the last administration of substance (on the 8th day after the start of treatment), blood is again taken from each animal by puncture of the retroorbital venous plexus for determination of the serum cholesterol. The blood samples are centrifuged and, after the serum is obtained, the cholesterol is determined by photometry using an EPOS analyser 5050 (Eppendorf-Gerätebau, Netheler & Hinz GmbH, Hamburg). The determination takes place with a commercially available enzyme assay (Boehringer Mannheim, Mannheim).

The effect of the test substances on the serum cholesterol concentration is determined by subtracting the cholesterol level in the 1st blood sample (initial value) from the cholesterol level in the 2nd blood sample (after treatment). The differences of all the cholesterol levels in a group are averaged and compared with the average of the differences in the control group.

Statistical analysis takes place using Student's t test after previous checking of the variants for homogeneity.

Substances which reduce the serum cholesterol in the treated animals compared with the control group statistically significantly (p<0.05) by at least 10% are judged as pharmacologically active.

Administration forms suitable for administering the compounds of the general formula (I) are all conventional ones, that is to say oral, parenteral, inhalation, nasal, sublingual, rectal or externals, such as, for example, transdermal, particularly preferably oral or parenteral. In connection with parenteral administration, particular mention should be made of intravenous, intramuscular, subcutaneous administration, for example as subcutaneous depot. Oral administration is very particularly preferred.

The active substances can in this connection be administered alone or in the form of preparations. Preparations suitable for oral administration are, inter alia, tablets, capsules, pellets, coated tablets, pills, granules, solid and liquid aerosols, syrups, emulsions, suspensions and solutions. The active substance must be present in an amount such that a therapeutic effect is achieved. In general, the active substance can be present in a concentration of from 0.1 to 100% by weight, in particular from 0.5 to 90% by weight, preferably from 5 to 80% by weight. The concentration of active substance should, in particular, be 0.5–90% by weight, that is, to say the active substance should be present in amounts sufficient to reach the stated dose range.

For this purpose, the active substances can be converted in a manner known per se into the customary preparations. This takes place by use of inert, nontoxic, pharmaceutically acceptable carriers, excipients, solvents, vehicles, emulsifiers and/or dispersants.

Examples of excipients which may be mentioned are: water, nontoxic organic solvents such as, for example, paraffins, vegetable oils (for example sesame oil), alcohols (for example ethanol, glycerol), glycols (for example polyethylene glycol), solid carriers such as natural, or synthetic ground minerals (for example talc or silicates), sugars (for example lactose), emulsifiers, dispersants (for example polyvinylpyrrolidone) and lubricants (for example magnesium sulphate).

In the case of oral administration, tablets can, of course, also contain additions such as sodium citrate together with additives such as starch, gelatin and the like. Aqueous preparations for oral administration may furthermore include flavour improvers or colorants.

The dosages administered on oral administration are preferably from 0.001 to 5 mg/kg, preferably 0.005 to 3 mg/kg, of body weight every 24 hours.

The novel active substances can be administered alone and, if required, also in combination with other active substances, preferably from the group of CETP inhibitors, antidiabetics, antioxidants, cytostatics, calcium antagonists, blood pressure-lowering agents, thyroid hormones, inhibitors of HMG-CoA reductase gene expression, inhibitors of HMG-CoA reductase, squalene synthesis inhibitors, ACAT inhibitors, perfusion-promoting agents, platelet aggregation inhibitors, anticoagulants, angiotensin-II receptor antagonists, cholesterol absorption inhibitors, MTP inhibitors, fibrates, niacin and PPAR agonists.

The following examples are intended to illustrate the invention by way of example without a restrictive effect on the scope of protection.

EXAMPLES

Starting Compounds

Example I 2,6-Dimethyl-4-nitrophenyl trifluoromethanesulphonate

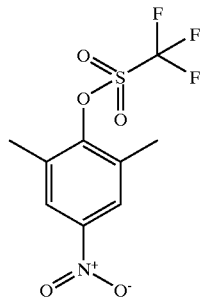

A solution of 150 g (0.9 mol) of dimethylnitrophenol in 700 ml of dichloromethane is cooled to −15° C. 181 ml of pyridine are added. 308.8 g (1.09 mol) of trifluoromethanesulphonic anhydride are then metered in dropwise over a period of 2 h in such a way that the reaction temperature does not exceed −5° C. Then, at a temperature of −5° C., 150 ml of water are added. The organic phase is extracted successively with HCl (1 molar, about 300 ml) and water (twice), each at 3–5° C. The solvent is removed in vacuo, and the residue is stirred with petroleum ether. The precipitate is filtered off with suction. A further fraction is obtained by cooling the mother liquor. Yield: 232 g (85%)

$^1$H-NMR (200 MHz, CDCl$_3$): 2.50, s, 6H; 8.04, s, 2H.

Example II

2-Bromo-1,3-dimethyl-5-nitrobenzene

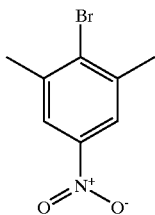

10.7 g (35.8 mmol) of 2,6-dimethyl-4-nitrophenyl trifluoromethanesulphonate (Example I) and 4.84 g (55.8 mmol) of LiBr are stirred in 120 ml of N-methylpyrrolidinone at 120° C. for 41 h. (Solvent: ethyl acetate/cyclohexane 1:4). After cooling, 80 ml of water are slowly added, and the mixture is stirred while cooling in an icebath for 1 h. The precipitate is filtered off with suction and stirred with 200 ml of petroleum ether. The solvent is removed in vacuo. 7.23 g (85%) of solid are obtained.

$^1$H-NMR (200 MHz, DMSO-D$_6$): 2.52, s, 6H; 8.02, s, 2H.

Example III

4-Bromo-3,5-dimethylaniline

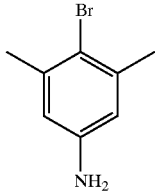

153 g of tin dichloro dihydrate (678 mmol) are added to 1.7 l of conc. HCl and heated to about 50° C. 26 g (113 mmol) of 2-bromo-1,3-dimethyl-5-nitrobenzene (Example II) are added. The suspension is heated at about 70° C. for 20 min. It is then allowed to cool slowly to room temperature. The precipitated white solid is filtered off and washed with cold acetone. The resulting hydrochloride is taken up in 1 N NaOH, briefly stirred and extracted 5 times with ethyl acetate. The organic phases are combined and dried over sodium sulphate, and the solvent is removed in vacuo.

$^1$H-NMR (200 MHz, DMSO-D$_6$): 2.19, s, 6H; 5.21, s, broad, 2H; 6.39, s, 2H

Example IV tert-Butyl 4-bromo-3,5-dimethylphenylcarbamate

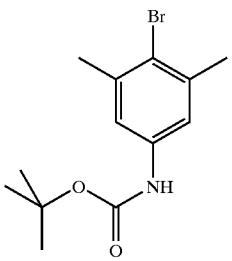

4 g (14.9 mmol) of 4-bromo-3,5-dimethylaniline (Example III) and 4.2 g (19.4 mmol) of di-tert-butyl pyrocarbamate are heated under reflux in 150 ml of THF for 5 hours. The solvent is removed in vacuo, the residue is taken up in ether and the solution is washed successively with 10% strength citric acid solution, sodium bicarbonate solution and water. The organic phase is dried over sodium sulphate, and the solvent is removed in vacuo. 4.3 g (95%) of tert-butyl 4-bromo-3,5-dimethylphenylcarbamate are obtained.

$^1$H-NMR (200 MHz, DMSO-D$_6$): 1.47, s, 9H; 2.28, s, 6H; 7.29, s, 2H; 9.39, s, 1H.

Example V tert-Butyl 4-[hydroxy(4-methoxy-3-isopropylphenyl)methyl]-3,5-dimethylphenylcarbamate

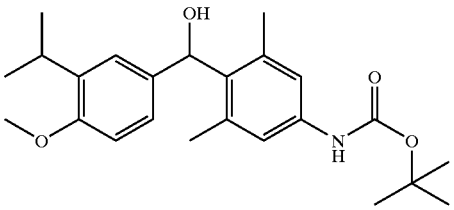

970 mg (3.23 mmol) of tert-butyl 4-bromo-3,5-dimethylphenylcarbamate (Example IV) are dissolved in 3 ml of cyclohexane and 3 ml of ether, cooled to −78° C., and added dropwise to 2.53 ml of 1.6 M methyllithium in ether at −78° C. After stirring at this temperature for 10 minutes, 3.8 ml of 1.7 M tert-butyllithium in pentane are added dropwise. The mixture is stirred at −78° C. for 1 hour and, after addition of 518 mg (2.9 mmol) of 3-isopropyl-4-methoxybenzaldehyde dissolved in 1 ml of ether/cyclohexane (1/1), stirred at −78° C. for 30 min and at room temperature for one hour. It is diluted with water and ether, the organic phase is washed with 10% strength citric acid solution, sodium bicarbonate solution and water and dried over sodium sulphate, and the solvent is removed in vacuo. Purification by chromatography (cyclohexane/ethyl acetate= 9:1) affords 0.76 g (53%) of tert-butyl 4-[hydroxy(4-methoxy-3-isopropylphenyl)methyl]-3,5-dimethylphenylcarbamate.

$^1$H-NMR (400 MHz, CDCl$_3$): 1.16, d, 3H; 1.20, d, 3H; 1.52, s, 9H; 2.05, d, 1H; 2.225, s, 6H; 3.28, hept, 1H; 3.81, s, 3H; 6.26, d, 1H; 6.40, s, 1H; 6.72, m, 1H; 6.90, dd, 1H; 7.06, s, 2H; 7.22, m, 1H.

Example VI
tert-Butyl 4-(4-methoxy-3-isopropylbenzyl)-3,5-dimethylphenylcarbamate

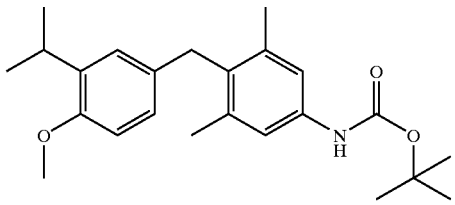

730 mg (1.66 mmol) of tert-butyl 4-[hydroxy(4-methoxy-3-isopropylphenyl)methyl]-3,5-dimethylphenylcarbamate (Example V) are hydrogenated with 700 mg of Pd/C (10%) and with 1 bar of hydrogen at RT for 4 hours. The mixture is filtered through kieselguhr, the solvent is removed in vacuo, and purification by chromatography results in 578 mg (91%) of tert-butyl 4-(4-methoxy-3-isopropylbenzyl)-3,5-dimethylphenylcarbamate.

$^1$H-NMR (400 MHz, CDCl$_3$): 1.18, d, 6H; 1.52, s, 9H; 2.21, s, 6H; 3.26, hept, 1H; 3.78, s, 3H; 3.92, s, 2H; 6.38, s, 1H; 6.63, m, 2H; 6.95, m, 1H; 7.08, s, 2H.

Example VII
4-(3-Isopropyl-4-methoxybenzyl)-3,5-dimethylaniline

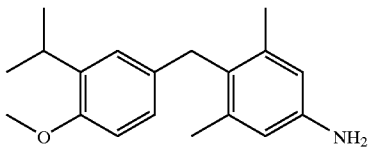

578 mg (1.36 mmol) of tert-butyl 4-(4-methoxy-3-isopropylbenzyl)-3,5-dimethylphenylcarbamate (Example VI) are dissolved in 10 ml of 5% trifluoroacetic acid in dichloromethane at 0° C. and stirred for 4 hours. The mixture is neutralized with sodium bicarbonate solution and dried over sodium sulphate. The product after removal of the solvent is reacted further without further purification.

$^1$H-NMR (400 MHz, CDCl$_3$): 1.16, d, 6H; 2.16, s, 6H; 3.26, hept, 1H; 3.78, s, 3H; 3.89, s, 2H; 6.45, m, 1H; 6.68, m, 1H; 6.95, s, 1H.

Example VIII
tert-Butyl 4-[[3-(4-fluorobenzyl)-4-methoxyphenyl](hydroxy)methyl]-3,5-dimethylphenylcarbamate

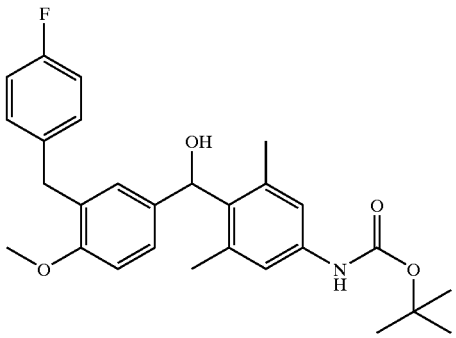

1.3 ml of methyllithium (2.1 mmol, 1.6 M in diethyl ether) are introduced into 1 ml of diethyl ether and, at -78° C., 600 mg (1.99 mmol) of tert-butyl 4-bromo-3,5-dimethylphenylcarbamate (Example IV) in 2 ml of diethyl ether/1 ml of THF are added. After 20 min, 1.53 ml of t-BuLi (2.6 mmol, 1.7 M in pentane) are added dropwise and the mixture is stirred at -78° C. for 30 min. 3-(4-Fluorobenzyl)-4-methoxybenzaldehyde dissolved in 3 ml of THF is added dropwise. After stirring at -78° C. for 1 h, aqueous NH$_4$Cl solution is added. The mixture is diluted with diethyl ether and extracted with water, and the organic phase is dried and concentrated in a rotary evaporator. Chromatography (cyclohexane/ethyl acetate=6:1) affords 493 mg (46%) of tert-butyl 4-[[3-(4-fluorobenzyl)-4-methoxyphenyl](hydroxy)methyl]-3,5-dimethylphenylcarbamate.

$^1$H-NMR (300 MHz, CDCl$_3$): 1.52, s, 9H; 2.21, s, 6H; 3.78, s, 3H; 3.90, d, 2H; 6.20, d, broad, 1H; 6.38, s, broad, 1H; 6.77, d, 1H; 6.90, m, 4H; 7.05, s, 2H; 7.10, m, 3H.

Example IX
tert-Butyl 4-[3-(4-fluorobenzyl)-4-methoxybenzyl]-3,5-dimethylphenylcarbamate

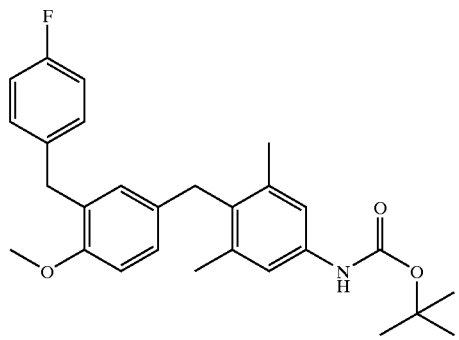

590 mg of tert-butyl 4-[[3-(4-fluorobenzyl)-4-methoxyphenyl](hydroxy)methyl]-3,5-dimethylphenylcarbamate (Example VIII), 24 mg of Pd/carbon (10%) and a drop of acetic acid are hydrogenated in 10 ml of methanol with hydrogen at atmospheric pressure for 4 h. The suspension is filtered through kieselguhr. The filtrate is concentrated in a rotary evaporator. Chromatography (cyclohexane/ethyl acetate=6:1) affords 449 mg (77%) of tert-butyl 4-[3-(4-fluorobenzyl)-4-methoxybenzyl]-3,5-dimethylphenylcarbamate.

$^1$H-NMR (300 MHz, CDCl$_3$): 1.52, s, 9H; 2.19, s, 6H; 3.72, s, 3H; 3.85, d, 4H; 6.72, m, 3H; 6.92, m, 2H; 7.05, m, 4H.

Example X
4-[3-(4-Fluorobenzyl)-4-methoxybenzyl]-3,5-dimethylaniline

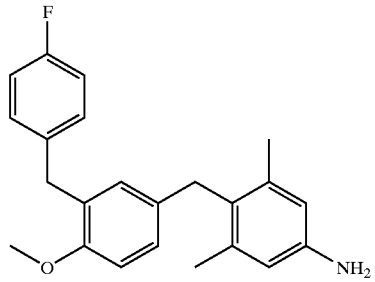

460 mg (1.02 mmol) of tert-butyl 4-[3-(4-fluorobenzyl)-4-methokybenzyl]-3,5-dimethylphenylcarbarnate (Example IX) are stirred in 10 ml of trifluoroacetic acid/ dichloromethane (10% strength solution) at room temperature overnight. After neutralization with NaHCO₃ solution, the organic phase is separated, dried over sodium sulphate and concentrated in a rotary evaporator. Chromatography (cyclohexane/ethyl acetate=6:1) affords 218 mg (55%) of 4-[3-(4-fluorobenzyl)-4-methoxybenzyl]-3,5-dimethylaniline.

¹H-NMR (300 MHz, CDCl₃): 2.22, s, 6H; 3.56, s, broad 2H; 3.74, s, 3H; 3.82, s, 2H; 3.85, s, 2H;

Exemplary Embodiments

Example 1

Ethyl 2-[4-(3-isopropyl-4-methoxybenzyl)-3,5-dimethylanilino]-2-oxoacetate

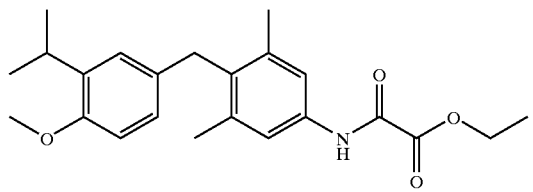

246 mg (0.86 mmol) of 4-(3-isopropyl-4-methoxybenzyl)-3,5-dimethylaniline (Example VII) are dissolved with 97 mg (0.96 mmol) of triethylamine in 10 ml of dichloromethane, and 160 mg (1.17 mmol) of ethoxalyl chloride are added dropwise. The mixture is stirred at room temperature for 4 hours, washed with sodium bicarbonate solution and water and dried over sodium sulphate, and the solvent is removed in vacuo. Purification by chromatography affords 128 mg (38%) of ethyl 2-[4-(3-isopropyl-4-methoxybenzyl)-3,5-dimethylanilino]-2-oxoacetate.

$R_f$=0.63 (toluene/acetonitrile=9:1).

Example 2

2-[4-(4-Hydroxy-3-isopropylbenzyl)-3,5-dimethylanilino]-2-oxoacetic acid

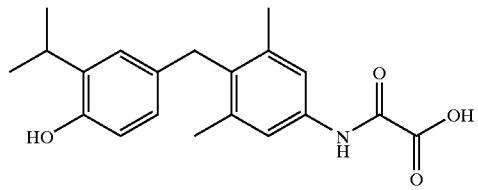

128 mg (0.33 mmol) of ethyl 2-[4-(3-isopropyl-4-methoxybenzyl)-3,5-dimethyl-anilino]-2-oxoacetate (Example 1) in 5 ml of dichloromethane at −78° C. under argon are treated dropwise with 167 mg (0.66 mmol) of boron tribromide. The reaction mixture is stirred at room temperature for 2.5 hours. It is poured into buffer of pH 7, the phases are separated, the aqueous phase is acidified with buffer of pH 4 and, after extraction with dichloromethane, the organic phases are combined. The solution is dried over sodium sulphate and the solvent is removed in vacuo. 112 mg (98%) of 2-[4-(4-hydroxy-3-isopropylbenzyl)-3,5-dimethylanilino]-2-oxoacetic acid are obtained.

¹H-NMR (400 MHz, CDCl₃): 1.21, d, 6H; 2.26, s, 6H; 3.15, hept, 1H; 3.95, s, 2H; 4.52, s, broad, 1H; 6.57, m, 2H; 6.91, m, 1H; 7.32, s, 2H; 8.83, s, broad, 1H.

Example 3

Ethyl ({4-[3-(4-fluorobenzyl)-4-methoxybenzyl]-3,5-dimethylphenyl}amino)(oxo)-acetate

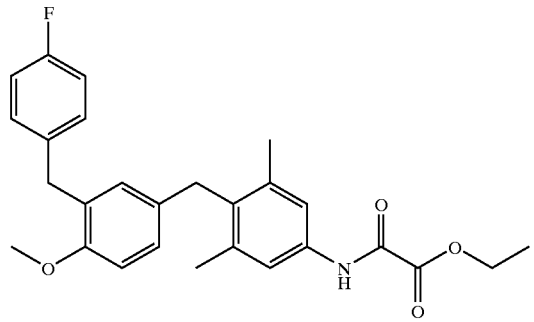

335 mg (0.96 mmol) of 4-[3-(4-fluorobenzyl)-4-methoxybenzyl]-3,5-dimethylaniline (Example X) and 107 mg (1.06 mmol) of triethylamine are introduced into ml of dichloromethane and, at 0° C., 177 mg (1.29 mmol) of ethoxalyl chloride are added dropwise. The mixture is stirred for 4 h. It is shaken with NaHCO₃ solution and NaCl solution, and the organic phase is dried and concentrated in a rotary evaporator. Purification by chromatography (cyclohexane/ethyl acetate=7:1) affords 231 mg of ethyl ({4-[3-(4-fluorobenzyl)-4-methoxybenzyl]-3,5-dimethylphenyl}amino)(oxo)-acetate.

¹H-NMR (400 MHz, DMSO-D₆): 1.21, t, 3H; 2.21, s, 6H; 3.42, quart, 2H; 3.74, s, 4H; 6.71, m, 2H; 6.92, m, 3H; 7.10, m 2H; 7.31, s, 2H; 8.73, s, 1H.

Example 4

({4-[3-(4-Fluorobenzyl)-4-hydroxybenzyl]-3,5-dimethylphenyl}amino)(oxo)acetic acid

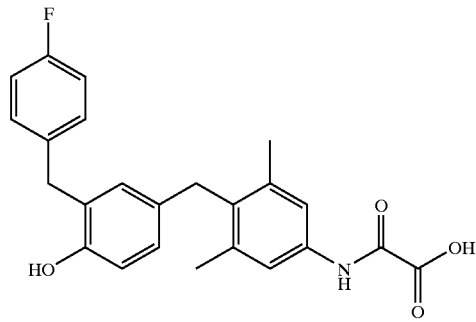

102 mg (0.22 mmol) of ethyl ({4-[3-(4-fluorobenzyl)-4-methoxybenzyl]-3,5-dimethylphenyl}amino)(oxo)acetate (Example 3) in 5 ml of dichloromethane at −78° C. under argon are treated slowly with 65 mg (0.25 mmol) of BBr₃. The reaction mixture is stirred overnight while reaching room temperature. It is again cooled to −78° C. and a further 65 mg (0.25 mmol) of BBr₃ is added. The mixture is stirred at room temperature for 2 hours. Pouring into ice-water, stirring for 2 hours, extraction with dichloromethane and ethyl acetate and drying over sodium sulphate are followed by concentration in a rotary evaporator. The residue is stirred with ether and the solid is filtered off with suction. 51 mg (48%) of ({4-[3-(4-fluorobenzyl)-4-hydroxy-benzyl]-3,5-dimethylphenyl}amino)(oxo)acetic acid are obtained.

¹H-NMR (400 MHz, DMSO-D₆): 2.12, s, 6H; 3.78, s, 4H; 6.61, m, 4H; 7.05, m, 2H; 7.18, m, 2H; 7.49, s, 2H; 9.20, s, 1H; 9.91, s, 1H.

Example 5

({4-[3-(4-Fluorobenzyl)-4-methoxybenzyl]-3,5-dimethylphenyl}amino)(oxo)acetic acid

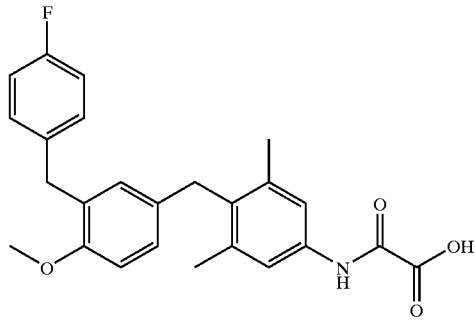

290 mg (0.64 mmol) of ethyl ({4-[3-(4-fluorobenzyl)-4-methoxybenzyl]-3,5-dimethylphenyl-}amino)(oxo)acetate (Example 3) in 8 ml of dichloromethane at −78° C. under argon are treated slowly with 356 mg (1.41 mmol) of BBr$_3$. The mixture is allowed to fall to room temperature and is stirred for 2.5 h. The reaction mixture is poured into buffer of pH 7, the organic phase is separated off, and the pH of the aqueous phase is adjusted to pH 7 and it is then extracted. The combined organic phases are washed with saturated NaCl solution, dried and concentrated in a rotary evaporator. The residue is stirred with diethyl ether, filtered off with suction and dried.

$^1$H-NMR (300 MHz, CDCl$_3$): 2.22, s, 6H; 3.75, s, 3H; 3.85, s, 2H; 3.92, s, 2H; 6.61, m, 3H; 6.91, m, 2H; 7.09, m, 2H; 7.30, s, 2H; 8.82, s, 1H.

What is claimed is:

1. Compounds of the general formula (I)

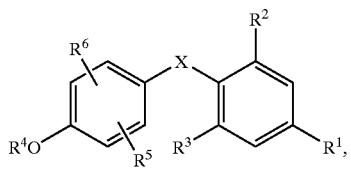

(I)

in which
X is CH$_2$, CHF or CF$_2$,
R$^1$ is a group of the formula

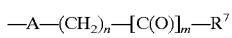

in which
A is CH$_2$, S, C(O) or NR$^8$,
n is the number 0, 1, 2 or 3,
m is the number 1 or 2,
  where m is the number 2 in the case where R$^2$ and R$^3$ are halogen,
R$^7$ is (C$_1$–C$_6$)-alkyl or a radical of the formula —NR$^9$R$^{10}$ or —OR$^{11}$,
  in which
  R$^8$, R$^9$, R$^{10}$ and R$^{11}$ are identical or different and are, independently of one another, hydrogen, (C$_1$–C$_6$)-alkyl or (C$_3$–C$_8$)-cycloalkyl,
R$^2$ and R$^3$ are identical or different and are halogen, (C$_1$–C$_6$)-alkyl, (C$_3$–C$_7$)-cycloalkyl, vinyl, CF$_3$, CHF$_2$ or CH$_2$F,
R$^4$ is hydrogen, (C$_1$–C$_6$)-alkyl or (C$_1$–C$_6$)-acyl,
R$^5$ is hydrogen, halogen, hydroxyl, cyano, CF$_3$, (C$_1$–C$_6$)-alkyl or (C$_1$–C$_6$)-alkoxy, R$^6$ is a radical of the formula

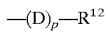

—(D)$_p$—R$^{12}$ in which
D is a group of the formula

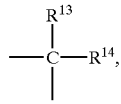

in which
R$^{13}$ and R$^{14}$ together are an oxo group or are identical or different and are hydrogen, halogen, hydroxyl, (C$_1$–C$_6$)-alkyl, (C$_1$–C$_6$)-alkoxy or a radical of the formula —NR$^{15}$R$^{16}$,
  in which
  R$^{15}$ and R$^{16}$ are identical or different and are hydrogen, benzyl, (C$_1$–C$_6$)-alkyl or (C$_3$–C$_8$)-cycloalkyl,
p is the number 0 or 1,
and
R$^{12}$ is hydrogen, OR$^{17}$, NR$^{18}$R$^{19}$, (C$_1$–C$_8$)-alkyl, (C$_3$–C$_8$)-cycloalkyl, (C$_6$–C$_{10}$)-aryl or a saturated, unsaturated or aromatic 5- to 10-membered heterocycle with up to three identical or different heteroatoms from the series of S, O and/or N,
where
the aforementioned hydrocarbon radicals and heterocycles may optionally be substituted once to three times, identically or differently, by substituents from the group of halogen, hydroxyl, oxo, cyano, nitro, amino, CF$_3$, (C$_1$–C$_6$)-alkyl, (C$_1$–C$_6$)-alkoxy, (C$_3$–C$_8$)-cycloalkyl, —O—C(O)—R$^{20}$, —C(O)—O—R$^{21}$, —C(O)—NR$^{22}$R$^{23}$ or —NH—C(O)—O—R$^{24}$,
and
in which
R$^{17}$, R$^{18}$, R$^{19}$, R$^{20}$, R$^{21}$, R$^{22}$, R$^{23}$ and R$^{24}$ are identical or different and are each, independently of one another, hydrogen, (C$_1$–C$_6$)-alkyl or (C$_3$–C$_8$)-cycloalkyl, each of which in turn may be substituted by hydroxyl, amino, mono- or di-(C$_1$–C$_6$)-alkylamino, phenyl, a saturated, unsaturated or aromatic 5- to 10-membered heterocycle with up to three identical or different heteroatoms from the series of S, O and/or N,
and the salts thereof.

2. Compounds of the formula (I) according to claim 1, in which
X is CH$_2$, CHF or CF$_2$,
R$^1$ is a group of the formula

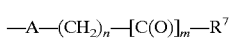

in which
A is CH$_2$, C(O) or NR$^8$,
n is the number 0, 1, or 2,
m is the number 1 or 2,
  where m is the number 2 in the case where R$^2$ and R$^3$ are halogen, or A is CH$_2$, and
  n is not the number 1 when A is NH and m is the number 1 and,
R$^7$ is a radical of the formula —NR$^9$R$^{10}$ or —OR$^{11}$,
  in which
  R$^8$, R$^9$, R$^{10}$ and R$^{11}$ are identical or different and, independently of one another, are hydrogen, (C$_1$–C$_6$)-alkyl or (C$_3$–C$_8$)-cycloalkyl, $R^2$ and $R^3$ are identical or different and are halogen, $(C_1-C_6)$-alkyl, cyclopropyl, vinyl, $CF_3$, $CHF_2$ or $CH_2F$, $R^4$ is hydrogen, $(C_1-C_3)$-alkyl or $(C_1-C_3)$-acyl, $R^5$ is hydrogen, halogen, $CF_3$, $(C_1-C_3)$-alkyl or $(C_1-C_3)$-alkoxy, $R^6$ is a radical of the formula

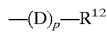

in which

D is a group of the formula

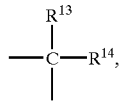

in which $R^{13}$ and $R^{14}$ together are an oxo group or are identical or different and are hydrogen, hydroxyl, $(C_1-C_6)$-alkyl, p is the number 0 or 1, and $R^{12}$ is hydrogen, $OR^{17}$, $NR^{18}R^{19}$, $(C_1-C_6)$-alkyl, $(C_3-C_8)$-cycloalkyl, $(C_6-C_{10})$-aryl or a saturated, unsaturated or aromatic 5- to 6-membered heterocycle with up to three identical or different heteroatoms from the series of S, O and/or N, where the aforementioned hydrocarbon radicals and heterocycles may optionally be substituted once to three times, identically or differently, by substituents from the group of halogen, hydroxyl, oxo, cyano, nitro, amino, $CF_3$, $(C_1-C_6)$-alkyl, $(C_1-C_6)$-alkoxy, $(C_3-C_8)$-cycloalkyl, —O—C(O)—$R^{20}$, —C(O)—O—$R^{21}$, —C(O)—$NR^{22}R^{23}$ or —NH—C(O)—O—$R^{24}$, and in which $R^{17}$, $R^{18}$, $R^{19}$, $R^{20}$, $R^{21}$, $R^{22}$, $R^{23}$ and $R^{24}$ are identical or different and are each, independently of one another, hydrogen, $(C_1-C_6)$-alkyl or $(C_3-C_8)$-cycloalkyl, each of which in turn may be substituted by hydroxyl, amino, mono- or di-$(C_1-C_6)$-alkylamino, phenyl, a saturated, unsaturated or aromatic 5- to 6-membered heterocycle with up to three identical or different heteroatoms from the series of S, O and/or N, and the salts thereof.

3. Compounds of the formula (I) according to claim 1, in which

X is $CH_2$, CHF or $CF_2$, $R^1$ is a group of the formula —NH—C(O)—C(O)—$OR^{11}$, in which $R^{11}$ is hydrogen or $(C_1-C_4)$-alkyl, $R^2$ and $R^3$ are identical or different and are halogen, $(C_1-C_4)$-alkyl, cyclopropyl, $CF_3$, $CHF_2$ or $CH_2F$, $R^4$ is hydrogen or $(C_1-C_3)$-alkyl, $R^5$ is hydrogen, and $R^6$ is $(C_1-C_6)$-alkyl or $(C_3-C_6)$-cycloalkyl or is a radical of the formula

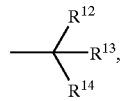

in which $R^{12}$ is phenyl, pyrimidinyl, pyridyl or 3(2H)-pyridazinonyl, each of which may be substituted up to three times, identically or differently, by halogen, hydroxyl, trifluoromethyl, $(C_1-C_3)$-alkyl or $(C_1-C_3)$-alkoxy, or is a radical of the formula —$NR^{18}R^{19}$, in which $R^{18}$ and $R^{19}$ are identical or different and are, independently of one another, $(C_1-C_4)$-alkyl which may be substituted by hydroxyl, amino, mono- or di-$(C_1-C_4)$-alkylamino, or by phenyl, pyridyl or pyrimidinyl, each of which is optionally substituted up to three times by hydroxyl, halogen, trifluoromethyl, methoxy or $(C_1-C_3)$-alkyl, $R^{13}$ and $R^{14}$ together are an oxo group or are identical or different and are hydrogen, hydroxyl, $(C_1-C_6)$-alkyl, and the salts thereof.

4. Process for preparing compounds of the general formula (I) as defined in claim 1, characterized in that reactive phenol derivatives of the general formula (II) are reacted with reactive phenyl derivatives of the general formula (III)

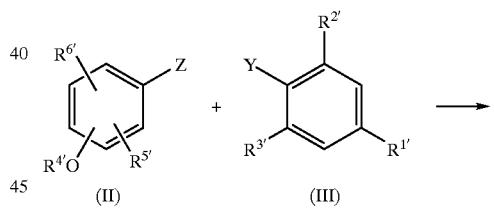

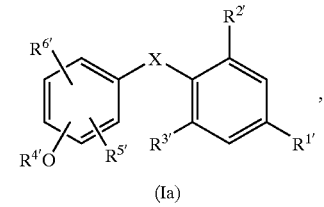

where the substituents $R^{1'}$, $R^{2'}$, $R^{3'}$, $R^{4'}$, $R^{5'}$ and $R^{6'}$ have the meanings stated for $R^1$ to $R^6$ in claim 1, and Z and Y are each groups of opposite reactivity, X' has the meaning stated for X in claim 1 or is

5. Compounds of the general formula (Ia)

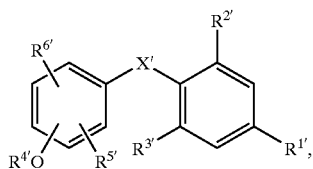
(Ia)

in which $R^{1\prime}$, $R^{2\prime}$, $R^{3\prime}$, $R^{4\prime}$, $R^{5\prime}$ and $R^{6\prime}$ have the meanings stated for $R^1$ to $R^6$ in claim 1, X' is —CH(OH)—, and the salts thereof.

6. Medicament containing at least one compound of the general formula (I) according to claim 1.

7. Process for producing medicaments, characterized in that at least one compound of the general formula (I) according to claim 1 is converted with excipients and carriers into a suitable administration form.

8. A method for the treatment and/or prophylaxis of arteriosclerosis and hypercholesterolaemia comprising administering to a subject in need thereof an effective amount of a compound according to claim 1.

9. A method for the prophylaxis and/or treatment of types of disorders which can be treated with natural thyroid hormone comprising administering to a subject in need thereof an effective amount of a compound according to claim 1.

10. The process of claim 4, wherein the intermediates of the general formula (Ia) in which X' is —CH(OH)— are isolated prior to reduction.

11. The method of claim 8, wherein a compound of claim 1 is administered in combination with other medicaments.

12. The method of claim 9, wherein a compound of claim 1 is administered in combination with other medicaments.

* * * * *